(12) United States Patent
Huss

(10) Patent No.: US 6,361,997 B1
(45) Date of Patent: Mar. 26, 2002

(54) GENETICALLY MODIFIED CD34-NEGATIVE ADHERENTLY GROWING STEM CELLS AND THEIR USE IN GENE THERAPY

(76) Inventor: Ralf Huss, Tegernseer Str. 78, 83666 Waakirchen (DE)

( * ) Notice: Subject to any disclaimer, the term of this patent is extended or adjusted under 35 U.S.C. 154(b) by 0 days.

(21) Appl. No.: 09/743,904

(22) PCT Filed: Jul. 22, 1999

(86) PCT No.: PCT/DE99/02309

§ 371 Date: Feb. 24, 2001

§ 102(e) Date: Feb. 24, 2001

(87) PCT Pub. No.: WO00/06705

PCT Pub. Date: Feb. 10, 2000

(30) Foreign Application Priority Data

Jul. 24, 1998 (DE) .......................................... 198 33 476

(51) Int. Cl.[7] .................................................. C12N 5/10
(52) U.S. Cl. ................. 435/372; 435/372.1; 435/372.2; 435/372.3
(58) Field of Search ........................... 514/44; 435/372, 435/372.1, 372.2, 372.3, 6

(56) References Cited

U.S. PATENT DOCUMENTS 5,691,176 A 11/1997 Lebkowski et al.

FOREIGN PATENT DOCUMENTS

| WO | WO 95/02038 | 1/1995 |
|----|-------------|--------|
| WO | 99/02309 | 2/2000 |

OTHER PUBLICATIONS

Clay et al., Pathology Oncology Research, vol. 5, No. 1 (1999), pp. 3–15.*
Huss, R. (1996) "Applications of Hematopoietic Stem Cells and Gene Transfer." *Infusionsther Transfusionsmed* 23:147–160.
Huss, R., et al. (1997) "CD34–Negative Hematopoietic Stem Cells Isolated from Human Peripheral Blood Cells as Ultimate Precursors of Hematopoietic Progenitors," *Infusionsther Transfusionsmed* 24:404–409.
Rolling, F. and Samulski R.J. (1995) "AAV as a Viral Vector for Human Gene Therapy." *Molecular Biotechnology* 3:9–15.
Verhasselt, B., et al. (1998) "Retrovirally Transduced CD34++ Human Cord Blood Cells Generate T Cells Expressing High Levels of the Retroviral Encoded Green Fluorescent Protein Marker In Vitro." *Blood* 91(2): 431–440.

* cited by examiner

*Primary Examiner*—James Ketter
(74) *Attorney, Agent, or Firm*—Barnes & Thornburg; Alice O. Martin

(57) ABSTRACT

The invention relates to the use of genetically modified, very early haematopoietic and mesenchymal stem cells (negative for the expression of the surface molecule CD34) in the individual gene therapy of mono- or oligogenetic diseases or in cell therapy. Autologous CD34-negative adherently growing stem cell cultures from the peripheral blood of the patient are applied and efficiently tranfected or infected with genetic constructs. The gene products of these genes should substitute defective or absent proteins or factors in the patient organism in the long term. After expansion, the autologous stem cells can also be used for cell therapy (organ replacement therapy).

2 Claims, 2 Drawing Sheets

GENETICALLY MODIFIED CD34-NEGATIVE ADHERENTLY GROWING STEM CELLS AND THEIR USE IN GENE THERAPY

DESCRIPTION OF THE INVENTION

The invention relates to the use of genetically modified earliest haematopoietic and mesenchymal stem cells (which are negative for the expression of the CD34 surface molecule) in individual gene therapy of mono- or oligogenetic diseases, respectively, diseases in blood formation as well as chronic disorders. For this purpose, endogenous CD34-negative adherently growing stem cell cultures are established from peripheral blood of the patient and efficiently transfected or infected, respectively, with gene constructs. On a long term basis, the gene products of said genes should substitute defective or missing proteins or factors in the patient organism, respectively, or enable a cell therapy.

The aim of somatic gene therapy or cell therapy, respectively, is the effective transfer of genetic material into the organism. In somatic gene therapy, genetic defects in body cells are corrected or genes encoding therapeutically useful gene products are introduced into cells. The gene-therapeutic alteration is not transmitted to the offspring. The introduction of genetic material into target cells may be done ex vivo as well as in vivo. Ex vivo means that the target cells are cultured outside of the body and are then reintroduced into the patient after introduction of the genetic material. However, the efficiency of somatic gene therapy is affected by the limited life of the transfected cells. Thus, cells having a particularly long life span are particularly suitable as the target cells for somatic gene therapy, such as haematopoietic stem cells. Heretofore, haeomatopoietic stem cells for transplantation purposes were obtained either from bone marrow of the donor or after enrichment steps from peripheral blood. The isolation of cells from the body of the patient or a near relative is referred to as allogenic bone marrow transplantation. Then, the frequently unselected mixture of stem cells and other bone marrow cells is reintroduced into the patient. Finally, the haematopoietic stem cells contained in said mixture migrate from the blood into the blood forming bone marrow to produce all cells of the blood forming system in a necessary amount. This type of transplantation is often associated with severe complications. Even the smallest tissue differences between donor and acceptor may result in highly dangerous complications for the patient. This risk must be weighed up against the actual disease, e.g. leukaemia. The donor-acceptor incompatibilities (graft versus host disease) are usually caused by cells contaminating the actual stem cell preparation. In particular, these are cells of the donor immune system.

To exclude this contamination of the bone marrow or stem cell transplant, respectively, methods have been developed to enrich the population of the haematopoietic stem cell. This cell which is also called pluripotent haematopoietic stem cell has been defined by the expression or non-expression of particular surface molecules so far. This pluripotent haematopoietic stem cell is able to produce the human haematopoietic cell lines—for example B cells, T cells, leukocytes, platelets or erythrocytes—via additional precursor cells. At the moment, the determination of a haematopoietic cell as a pluripotent haematopoietic stem cell is defined by the expression of the so-called CD34 molecule and simultaneously by the non-expression of other surface molecules, such as CD5. The CD34 molecule is a strongly negatively charged proteoglycane of the mucine family with a molecular weight of about 105 to 120 kD. Cellpro Inc. company, Seattle, USA, has developed a method for the purification of CD34 positive cells by means of an affinity chromatography (U.S. Pat. Nos. 5,215,927, 5,262,334, 5,240,856, 5,225 353, EP 526,577 B and EP 260,280 B). Simultaneously, CD34-negative cells form the pool for mesenchymal stem cells.

At the moment, for somatic gene therapy by means of haematopoietic stem cells CD34-positive cells are isolated from peripheral blood of the patient after stimulation of said cells with growth factors, e.g. G-CSF (Neupogen-R), and are reintroduced after genetic manipulation into the patient to reconstitute the lethally irradiated and chemotherapeutically treated bone marrow. Up to now, haematopoietic stem cells modified in this manner have been employed in particular for specific immune deficiency syndromes, such as adenosine desaminase defect, SCID syndrome or HIV infection, for metabolic diseases, such as Morbus Gaucher, in disorders of the blood formation, e.g. specific forms of thalassaemia and in malignant diseases, such as leukaemia.

Due to ethical and social reasons, this method is however restricted to the autologous or blood stem cell donation by near relatives, since for the accumulation of the stem cells in peripheral blood a growth factor has to be administered to the donor or patient, respectively. Up to now, it was not possible to predict the long term effect of said growth factor on a possible expansion of a leukaemia clone or a possible transformation of a healthy blood stem cell.

Furthermore, the somatic gene therapy by means of haematopoietic stem cells causes certain technical difficulties. Only a small portion of the haematopoietic stem cells transfected with therapeutic genes or gene constructs receives the genetic modification or no gene product will be produced. Thus, the efficiency of said method is very low at the moment; c.f. Huss, R. Infusionsthera. Transfusionsmed. 23 (1996) 147–160.

There is the need to provide improved means and methods which may be used in gene therapy.

The object is solved by the subject matters mentioned in the claims.

Thus, the subject matter of the invention are genetically modified CD34 negative adherently growing stem cells.

In a preferred embodiment the life span or the ability to divide, respectively, is prolonged by transient immortalization.

The invention is described in more detail by FIGS. 1 and 2 and the following description.

DETAILED DESCRIPTION OF THE INVENTION

Figure 1:
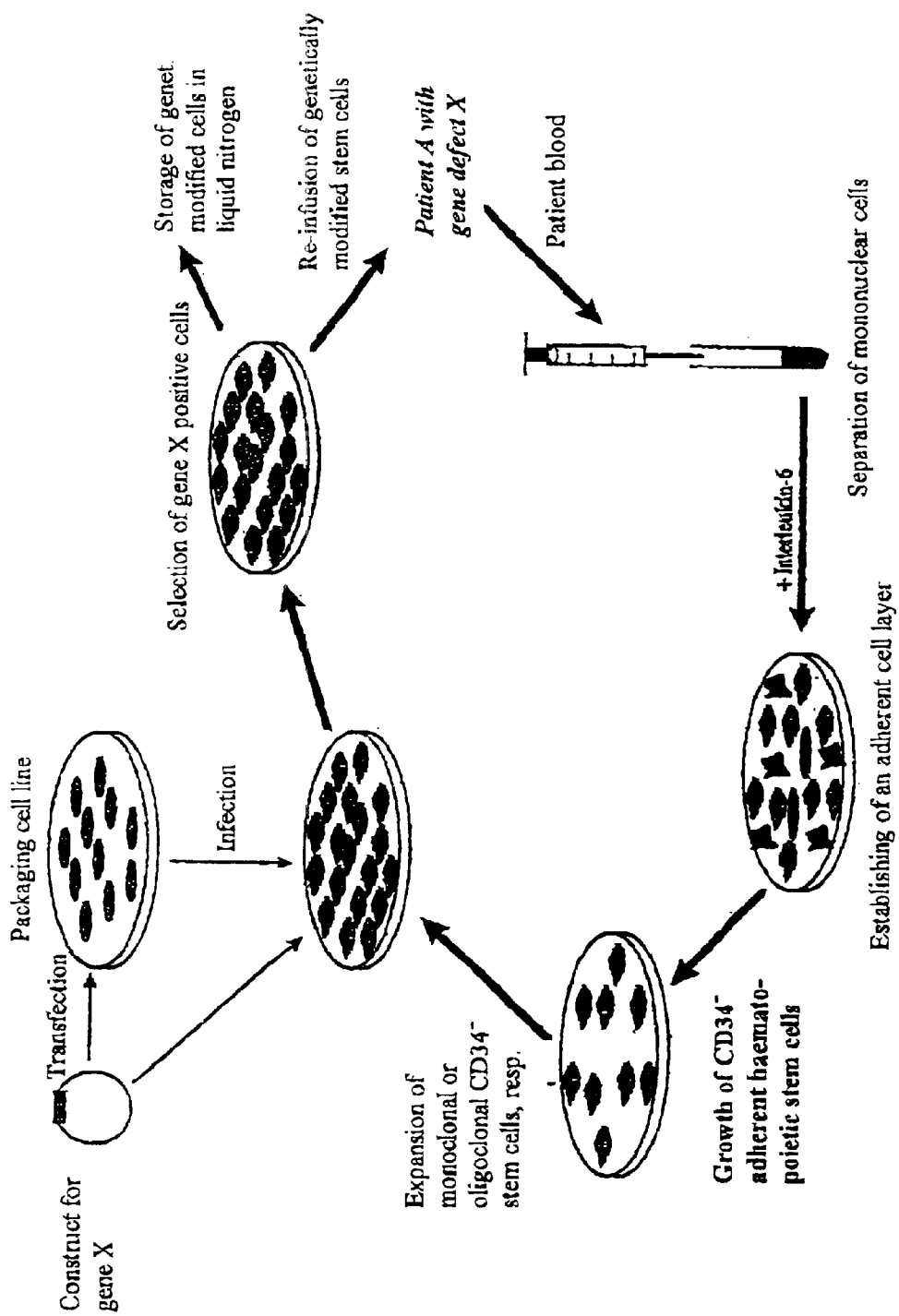
FIG. 1 shows a schematic illustration of the infection of target cells isolated from the patient.

The initial observation of the existence of earliest CD34-negative haematopoietic stem cells is based on the isolation and cloning of a corresponding cell line from canine primary bone marrow stroma cultures consisting of CD34 negative cells which are similar to fibroblasts and are in particular able to produce haematopoietic growth factors. Until now, the production of haematopoietic growth factors has already been described for stromal cell lines (see DE 4322570 C1). From such a primary culture, monoclonal populations (colony forming units=CFU) have been established in a standard colony assay. Some of said clones were able to differentiate to more mature haematopoietic precursor cells (Huss et al., Proc. Natl. Acad. Sci. USA 92 (1995) 748–752). Differentiation as well as proliferation of said cells is dependent on different growth factors. Thus, stem cell factor (c-kit ligand; SCF) induces the differentiation of CD34 negative adherently growing cells to CD34 positive cells no longer growing adherently, while interleukin 6 (IL-6) primarily promotes the proliferation and adherent growth (Huss et al., Blood 85 (1995) 2414–2421).

From CD34-positive cells of peripheral blood, a CD34-negative adherently growing population which is similar to fibroblasts could be established. It has been found that the procedure of differentiation from CD34-negative, adherent growth to CD34-positive, no longer adherent growth was reversible. By the addition of IL-6 an adherent but initially non-homogenous cell population has been established from peripheral mononuclear cells of healthy voluntary donors. For this purpose about 20 ml of heparinized blood were loaded twice on a Ficoll gradient, the mononuclear cell fraction was isolated according to standard methods and added to IL-6 containing medium in cell culture flasks in an incubator at 37° C. and 5% of $CO_2$. After a few days an adherently growing cell layer was produced. This primary culture initially consisted of cells similar to fibroblasts, as well as macrophages, endothelial cells and occasional fat cells, as detected by means of immune phenotyping. However, the amount of the "contaminating" cells, decreased completely during the first days and weeks (Huss et al., Infusionsthera. Transfusionsmed. 24 (1997) 404–409), until a nearly homogenous cell population was formed. However, at this point it is not possible to clone said population, since it has not been immortalized. Nevertheless, said cells may be maintained in cell culture or frozen in liquid nitrogen in a usual manner.

By modifying the conditions in the cell culture CD34-negative adherently growing cells may also differentiate to mesenchymal stem cells and thus produce a precursor cell for bone, cartilage and other tissues.

Gene Transfer

CD34-negative adherently growing cells similar to fibroblasts were isolated from purified mononuclear cells of peripheral blood according to the above method. Initially there was a high contamination with other cells which however completely disappeared in the course of time such that 100% of the adherent cells present were CD34 negative adherent cells. For an optimal transduction efficiency different methods for gene transfer of "green-fluorescence protein" (GFP) were investigated. The "green-fluorescence protein" is a gene construct which in transfected or infected cells, respectively, shines green under ultraviolet light and thus enables the detection of a cell transfected or infected, respectively, with GFP in a simple manner.

The results with in-vitro cultures as well as in-vivo experiments in SCID mice (SCID mice have a cellular immune deficiency enabling the mice to serve as an in-vivo model for allogenic or xenogenic transplantation models) have shown, that expression of GFP in the target cells lasts several weeks wherein the fluorescence of GFP transfected cells in SCID mice is clearly visible but weaker than in the plain cell culture method.

The investigation of different transfection or infection methods, respectively, for the GFP protein gave different results:

The $CaCl_2$ procedure for the transfection induced a strong cellular stress leading to the death of a large portion of the cells to be transfected.

In contrast, the efficiency of the gene transfer by means of Lipofectamine or infection with viral supernatant, respectively, was very high. While the transfection efficiency with lipofectamine after one application was about 40–50%, the infection efficiency with viral supernatant after 10 to 14 days and 3–4 passages was 88–94%. Correspondingly, new virus-containing supernatant was added to the target cells every 3–4 days.

TABLE

|  | % GFP-positive | repetition | % dead cells |
|---|---|---|---|
| transfection with $CaCl_2$ | 68 ± 17 | no | 40 ± 21 |
| transfection with lipofectamine | 47 ± 6 | no | <5 |
| Infection with viral supernatant | 91 ± 5 | yes | <1% |

Efficiency

The obvious advantages of the system of the invention is the high transfection or infection efficiency of this homogenous cell population which mostly is not yet monoclonal but often oligoclonal.

While similar methods despite intensive efforts have an infection efficiency of about 5–20% of haematopoietic precursor cells, nearly all cells of the early stem cell population of the present invention are infected with the desired gene.

Experiments with SCID mice have shown that the expression of the gene also occurs in vivo in all lines of haematopoiesis. This is not only valid for retroviral constructs but also for the application of adenovirus-associated viruses (AAV) or constructs derived from Epstein-Barr virus (EBV).

Homogeneity

Due to their simple isolation from peripheral blood and their high efficiency, the adherently growing nearly homogenous cell populations similar to fibroblasts are excellently applicable in the fields of gene therapy and cell therapy.

Experiments have shown that said earliest haematopoietic stem cells may not only show long-term reconstitution but may also induce a tolerance via their colonization in the thymus.

This allows an application not only in the autologous or syngeneic system but also in the field of allogenic transplantation.

Therapy Options

All genes representing a gene product which is defective or missing in the patient may be reintroduced into the patient with his own genetically modified cells by infection of autologous haematopoietic cells with a construct for the missing or defective gene (see FIG. 1).

Candidates are in particular genes involved in certain metabolic diseases (e.g.

M. Gaucher, PNH, diabetes mellitus), in immune deficiency syndromes (ADA deficiency, SCID, CGD, LAD, AIDS), haemoglobinopathies (e.g. sickle cell anaemia, thalassaemia) and malignant diseases (e.g. MDR, antisense constructs, hammerhead ribozymes in the case of identified mutations) (see also Table 1, page 8: Somatic Gene Therapy; P. L. Chang (ed.) CRC Press, Inc., Boca Raton, USA).

After transfer of the desired gene into the autologous early haematopoietic stem cells of the patient, the cells isolated from the patient may be frozen in liquid nitrogen to use them for the first time or again, as required. This is possible since said cells proliferate very extensively.

A further embodiment relates to the introduction of a "suicide-gene", for example thymidine kinase, to optionally eliminate said infected cells completely or partially by means of ganciclovir. By this, the cells may be maintained under continued growth control in vivo, e.g. if the activity of an enzyme exceeds the serum level desired or the tumor disease is cured.

Figure 2:
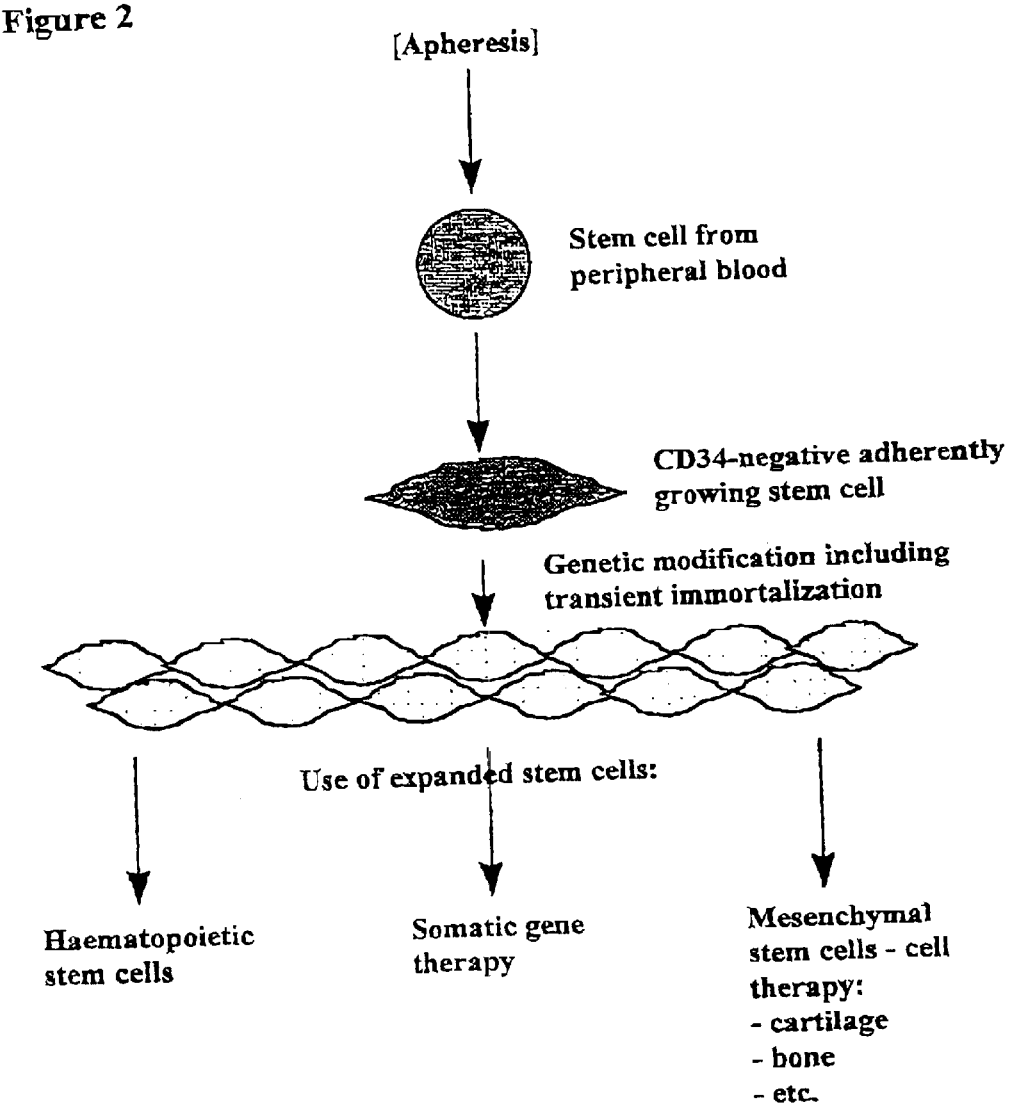
FIG. 2 shows uses of the expanded stem cells.

The stem cells partially immortalized in a transient (passager) manner may also be used for cell therapy or for the preparation of endogenous cartilage or bone substance, respectively (see FIG. 2).

In this embodiment there is also no need to subject the patient to a myeloablative therapy, since the haematopoiesis of the patient need not be completely reconstituted but only a part of the haematopoietic stem cells is substituted by genetically modified stem cells.

The following examples illustrate the invention.

EXAMPLE 1

Isolation of Cells

About 20 ml of heparinized blood or citrate blood are removed from the patient or the voluntary donor, respectively and layered over a Ficoll Hypaque gradient (Pharmacia Biotech, Uppsala, Sweden) (see also Huss et al., Infusionsthera. Transfusionsmed. 24 (1997) 404–409).

After 15–20 min of centrifugation at 400×g without braking the ring of mononuclear cells is removed and washed several times in PBS or isotonic saline.

Afterwards $5\times10^6$ to $1\times10^7$ cells/ml are incubated in a cell culture flask (e.g. NUNC) in cell culture medium (e.g. McCoy's standard medium with 12.5% fetal calf serum and 12.5% equine serum) in an incubator at 37° C. and 5% $CO_2$ in the presence of 10 ng/ml recombinant interleukin-6 (rhu IL-6; RD Systems GmbH, Wiesbaden).

The cultures were monitored daily and counted weekly.

After 10–14 days a homogenous cell population of adherently growing cells similar to fibroblasts arises which are nearly completely CD34 negative according to FACScan analysis or immune histochemistry, respectively. Nevertheless, some differentiating cells temporarily express CD34 antigen, since these cells are not synchronized.

EXAMPLE 2

Retroviral Infection/illustrated by the Infection with EBV Constructs

Said homogenous cell population described above is now incubated with retroviral supernatant of the PG-13 cell line (a packaging cell line which packages the desired retroviral vector after transfection of the PG-13 cells into a gibbon ape leukaemia virus envelope. The transfection of the packaging cell line is done by mixing 2,5 $\mu$g plasmid DNA with 15 $\mu$l Superfect (Qiagen) and incubating in 100 $\mu$l serum-free medium at room temperature for 20 min. Thereafter, this mixture is incubated with the PG-13 cells at 37° C. for 5 hours followed by the addition of new serum-containing medium) also over a period of 10–14 days during which time the virus-containing medium should be changed for at least three to four times. After this period the gene expression is investigated in the target cells (for GFP by means of fluorescence microscopy) and the efficiency is determined.

The positive cells may now be reintroduced into the patient or frozen for a later use. In these retroviral infections the MOI (Multiplicity of Infection=how much virus particles are necessary for infection of a cell) is about 10.

The cells may also be transiently immortalized to achieve an expansion of the stem cells.

EXAMPLE 3

Infection of the Target Cells Isolated from the Patient with Recombinant AAV Virus Expressing Luciferase The target cells isolated from the patient could be infected very efficiently also with recombinant AAV virus expressing luciferase. The target cells of the patient were incubated with LUC-rAAV at 37° C. for 3 hours and thereafter maintained in serum-free medium for additional 72 hours. Thereafter, both the luciferase activity and the luminescence were measured. In this system the MOI is about 1000.

EXAMPLE 4

Patient Example 1

The procedure is illustrated schematically in FIG. 1.

Blood is removed from the arm vein of patient A having the gene defect X and peripheral mononuclear cells are isolated therefrom by means of gradient centrifugation. These mononuclear cells are incubated in cell culture with interleukin-6, until an adherent cell layer has been established.

In the primary culture the contamination with non-haematopoietic stem cells is still very high. After 2 to 4 weeks exclusively CD34 negative haematopoietic stem cells are grown which may now be expanded.

These are now infected with retroviral virus constructs or AAV viruses which have been transfected with the desired gene construct before. After a few days the presence of gene X and the expression of gene product X (e.g. glucocerebrosidase or insulin) may be detected in the haematopoietic stem cells of patient A.

Now patient A receives his genetically modified early haematopoietic stem ells via infusion while a portion of said cells is stored in liquid nitrogen for later use. The blood stem cells of the patient which are provided with a new genetic information provide patient A with gene product X which is important for him.

In the case of diabetes mellitus it is enough to provide only a very low percentage of endogenous stem cells with the new genetic material to achieve a decrease in the blood sugar level and thus the necessary need for insulin. In diabetes patients this would delay or even prevent the severe concomitant diseases on a long term basis.

EXAMPLE 5

Patient Example 2

Patient B suffers from a severe cartilage defect in the knee-joint. Peripheral blood stem cells are removed from the patient (e.g. by means of apheresis) and transiently (passager) immortalized (e.g. by SV40 Large-T antigen in a cre/lox system with EBNA1). These cells are then differentiated to cartilage/bone precursor cells in cell culture and transplanted to the defective site.

What is claimed is:

1. Genetically modified CD34-negative adherently growing stem cells.

2. Genetically modified CD34-negative adherently growing stem cells according to claim 1, further comprising a construct selected from the group consisting of a retroviral construct an EBV construct and an adenovirus-associated construct.

* * * * *